United States Patent
Sawa et al.

(10) Patent No.: US 10,292,980 B2
(45) Date of Patent: May 21, 2019

(54) GAPDH CASCADE INHIBITOR COMPOUNDS AND METHODS OF USE AND TREATMENT OF STRESS INDUCED DISORDERS INCLUDING MENTAL ILLNESS

(71) Applicants: THE JOHNS HOPKINS UNIVERSITY, Baltimore, MD (US); SHOWA PHARMACEUTICAL UNIVERSITY, Tokyo (JP)

(72) Inventors: Akira Sawa, Baltimore, MD (US); Elki Takimoto, Baltimore, MD (US); Neelam Shahani, Baltimore, MD (US); David Kass, Columbia, MD (US); Toshiaki Saito, Saitama (JP)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/375,228

(22) Filed: Dec. 12, 2016

(65) Prior Publication Data

US 2017/0087145 A1 Mar. 30, 2017

Related U.S. Application Data

(62) Division of application No. 14/423,727, filed as application No. PCT/US2013/055524 on Aug. 19, 2013, now abandoned.

(60) Provisional application No. 61/693,266, filed on Aug. 25, 2012.

(51) Int. Cl.
*A61K 31/472* (2006.01)
*A61K 45/06* (2006.01)
*C07D 217/06* (2006.01)
*C07D 217/04* (2006.01)
*C07D 217/24* (2006.01)

(52) U.S. Cl.
CPC ........... *A61K 31/472* (2013.01); *A61K 45/06* (2013.01); *C07D 217/04* (2013.01); *C07D 217/06* (2013.01); *C07D 217/24* (2013.01)

(58) Field of Classification Search
CPC .................................................. A61K 31/472
See application file for complete search history.

(56) References Cited

U.S. PATENT DOCUMENTS

| | | | |
|---|---|---|---|
| 6,503,502 B1 | 1/2003 | Telerman et al. | |
| 7,211,585 B2 * | 5/2007 | Jover ................... | C07D 217/04 514/307 |
| 7,872,097 B2 | 1/2011 | Neya et al. | |
| 2004/0087531 A1 | 5/2004 | Telerman et al. | |
| 2005/0070015 A1 | 5/2005 | Nakamura et al. | |
| 2005/0221303 A1 | 10/2005 | Telerman et al. | |
| 2006/0084647 A1 | 4/2006 | Wang et al. | |
| 2007/0185196 A1 | 7/2007 | Reed et al. | |
| 2010/0210521 A1 | 8/2010 | Liu | |
| 2011/0021440 A1 | 1/2011 | Martin et al. | |
| 2011/0136697 A1 | 6/2011 | Morgan et al. | |
| 2011/0212956 A1 | 9/2011 | Danysz et al. | |

(Continued)

FOREIGN PATENT DOCUMENTS

EP     1592684 B1    7/2008

OTHER PUBLICATIONS

Antkiewicz-Michaluk et al. 1-methyl-1,2,3,4-tetrahydroisoquinoline protects against rotenone-induced mortality and biochemical changes in rat brain. European journal of pharmacology 466, 263-269 (2003).
Antkiewicz-Michaluk et al. Protective effect of 1-methyl-1,2,3,4-tetrahydroisoquinoline against dopaminergic neurodegeneration in the extrapyramidal structures produced by intracerebral injection of rotenone. The international journal of neuropsychopharmacology 7, 155-163 (2004).
Antkiewicz-Michaluk et al., Both stereoselective (R)- and (S)-1-Methyl-1,2,3,4-tetrahydroisoquinoline enantiomers protect striatal terminals against rotenone-induced suppression of dopamine release. Neurotoxicity research 20, 134-149 (2011).

(Continued)

*Primary Examiner* — Sahar Javanmard
(74) *Attorney, Agent, or Firm* — Johns Hopkins Technology Ventures

(57) ABSTRACT

In DN-DISC1 mice, a mouse model for major mental illnesses, the model that expresses pathological phenotypes relevant to schizophrenia, mood disorders, and addiction simultaneously, the inventors of the present invention found pronounced levels of oxidative stress in the prefrontal cortex, but not in the striatum. These mice also displayed greater amounts of GAPDH-Siah1 binding, a protein-protein interaction that is activated under exposure to oxidative stress. The present inventors investigated the role of oxidative stress in other organ systems. As detailed herein, the inventors found that GAPDH-Siah1 binding was increased in mouse models of cardiac failure. It was also found, that certain novel analogs of deprenyl, significantly inhibited GAPDH-Siah1 binding in cardiac tissue. Thus, with experimental data provided herein, it is clear that this GAPDH-Siah1 binding cascade is a crucial mechanism involved in major mental illness, such as schizophrenia, mood disorders, and addiction, as well as in stress-associated diseases involving other organs where GAPDH is expressed.
The present invention provides compounds and composition comprising analogs of deprenyl and their use in the inhibition of nuclear GAPDH-Siah1 binding and the activation of p300 and MEF2. Also provided herein are methods of prevention and treatment of stress induced disorders of the body, including, for example, major mental illness, such as schizophrenia, mood disorders, and addiction, as well as in stress-associated diseases involving other organs, such as cardiac hypertrophy, in vivo, comprising administering to a mammal a therapeutically effective amount of analogs of deprenyl.

1 Claim, 9 Drawing Sheets

(56) References Cited

U.S. PATENT DOCUMENTS

2011/0243968 A1  10/2011  Harris et al.

OTHER PUBLICATIONS

Waldmeier et al., Neurorescuing effects of the GAPDH ligand CGP 3466B. Journal of neural transmission. Supplementum, 197-214 (2000).

Tatton et al., Neuroprotection by deprenyl and other propargylamines: glyceraldehyde-3-phosphate dehydrogenase rather than monoamine oxidase B. Journal of neural transmission 110, 509-515 (2003).

Wasik et al., The effect of an endogenous compound 1-methyl-1,2,3,4-tetrahydroisoquinoline on morphine-induced analgesia, dependence and neurochemical changes in dopamine metabolism in rate brain structures., (2007) Journal of Physiology and Pharmacology, 58(2), 235-252.

Johnson et al., Cognitive and motivational deficits together with prefrontal oxidative stress in a mouse model for neuropsychiatric illness., (2013) Proc Natl Acad Sci U S A, 110(3), 12462-7.

Takimoto et al., Chronic inhibition of cyclic GMP phosphodiesterase 5A prevents and reverses cardiac hypertrophy, (2005) Nature Medicine, 11, 214-222.

Takimoto et al., Regulator of G protein signaling 2 mediates cardiac compensation to pressure overload and antihypertrophic effects of PDE5 inhibition in mice., (2009) J Clin Invest., 119(2), 408-420.

Zhang et al., Myocardial Remodeling is Controlled by Myocyte-targeted Gene Regulation of Phosphodiesterase—Type-5., (2010) J Am Coll Cardiol, 56(24), 2021-2030.

Wei et al., Quantitative Control of Adaptive Cardiac Hypertrophy by Acetyltransferase p300., (2008) Circulation, 118, 934-946.

Hara et al., S-nitrosylated GAPDH initiates apoptotic cell death by nuclear translocation following Siah1 binding., (2005) Nat Cell Biol, 7(7), 665-674.

Patsenka et al., Inhibition of rodent brain monoamine oxidase and tyrosine hydroxylase by endogenous compounds—1,2,3,4-tetrahydroisoquinoline alkaloids. Polish journal of pharmacology 56, 727-734 (2004).

Kohno et al., Tetrahydroisoquinoline and 1-methyl-tetrahydroisoquinoline as novel endogenous amines in rat brain. Biochemical and biophysical research communications 140, 448-454 (1986).

Nagatsu et al., Molecular mechanism of the relation of monoamine oxidase B and its inhibitors to Parkinson's disease: possible implications of glial cells. Journal of neural transmission. Supplementum, 53-65 (2006).

Hara et al., Neuroprotection by pharmacologic blockade of the GAPDH death cascade. Proceedings of the National Academy of Sciences of the United States of America 103, 3887-3889, (2006).

Sen et al. GOSPEL: a neuroprotective protein that binds to GAPDH upon S-nitrosylation. Neuron 63, 81-91 (2009).

Kragten et al., Glyceraldehyde-3-phosphate dehydrogenase, the putative target of the antiapoptotic compounds CPG 3466 and R-(−)-deprenyl. The Journal of biological chemistry 273, 5821-5828 (1998).

Katagiri, N. et al., "Preventative effects of 1,3-dimethyl- and 1,3-dimethyl-N-propargyl-1,2,3,4-tetrahydroisoquinoline on MPTP-induced Parkinson's disease-like symptoms in mice" Brain Research vol. 1321 (2010) pp. 133-142.

Pietraszek, M., et al., "1-Methyl-1,2,3,4-tetrahydroisoquinoline Antagonizes a Rise in Brain Dopamine Metabolism, Glutamate Release in Frontal Cortex and Locomotor Hyperactivity Produced by MK-801 but not the Disruptions of Prepulse Inhibition, and Impairment of Working Memory in Rat" Neurotox Res (2009) vol. 16, pp. 390-407.

Kitabatake, M., et al., "Facile synthesis and in vitro properties of 1-alkyl- and 1-alkyl-N-propargyl-1,2,3,4-tetrahydroisoquinoline derivatives on PC12 cells", European Journal of Medicinal Chemistry (2009) vol. 44, pp. 4034-4043.

Toda, J., et al., "A chiral synthesis of four stereoisomers of 1,3-dimethyl-1,2,3,4-tetrahydroisoquinoline, an inducer of parkinson-like syndrome" Chem. Pharm. Bull (2000) vol. 48, No. 1, pp. 91-98.

Kaidanovich-Beilin, O., et al., (2011). Assessment of Social Interaction Behaviors. JoVE. 48. http://www.jove.com/details.php?id=2473, doi: 10.3791/2473.

* cited by examiner

IMMUNOFLUORESCENCE

GAPDH CASCADE INHIBITOR COMPOUNDS AND METHODS OF USE AND TREATMENT OF STRESS INDUCED DISORDERS INCLUDING MENTAL ILLNESS

REFERENCE TO RELATED APPLICATIONS

This application is a Divisional of U.S. Ser. No. 14/423,727, filed Feb. 25, 2015, which is a 35 U.S.C. § 371 U.S. national entry of International Application PCT/US2013/055524, having an international filing date of Aug. 19, 2013, which claims the benefit of U.S. Provisional Application No. 61/693,266, filed Aug. 25, 2012, the content of each of the aforementioned applications is herein incorporated by reference in their entirety.

BACKGROUND OF THE INVENTION

Proper environmental stimuli are required to maintain homeostasis of organs and living organisms, whereas excess stressors disrupt such homeostasis. The underlying mechanism involves in nuclear factors and gene transcription, where histone acetyltransferases (HATs) play an essential role. The enzyme p300 is a representative HAT that is essential for maintenance of the organ function of heart and brain, while it is also implicated in the pathogenesis. Thus, it is an essential biological question how p300 activity is influenced by environmental and intrinsic factors, such as stress, to mediate physiology or pathophysiology.

The inventors have previously reported that a unique pool of glyceraldehyde-3-phosphate dehydrogenase (GAPDH) activate p300, when GAPDH is oxidized/S-nitrosylated and translocated with E3 ubiquitin-protein ligase (Siah1) into the nucleus upon exposure to stressors: in this cascade, only a few percentage of GAPDH converted to a signaling molecule due to this specific posttranslational modification, and overall change in cytosolic and glycolytic GAPDH is negligible.

It has long been noted that the cognitive impairments in patients with schizophrenia point to dysfunction of the frontal lobe. These abnormalities are found throughout the lifespan of affected individuals, suggesting a neurodevelopmental basis, which is consistent with alterations in frontal lobe structure in some cases. At autopsy, neuropathology in schizophrenia affecting synaptic and cellular integrity has directed an increasing focus on prefrontal-dependent behaviors in preclinical models for this disease.

Because cortical asynchrony can contribute to the kinds of cognitive deficits found in patients, the failure of mechanisms needed for synchronous cortical activity, such as dysfunction of interneurons, are of particular interest. In that context, studies on autopsied brains from patients with schizophrenia show a decrease in parvalbumin immunoreactivity, a relevant marker for fast-spiking interneurons that regulate synchonous cortical activity. One possible cause of impaired integrity affecting that interneuron population comes from evidence that decreased parvalbumin immunoreactivity is elicited by oxidative stress in mouse models relevant to schizophrenia. Further supporting such a basis for prefrontal dysfunction, analysis of cerebrospinal fluid from recent-onset patients with schizophrenia has indicated the presence of oxidative stress.

Stress is known to affect all of the organ systems of the body. In another example, the heart develops hypertrophy to pathological stressors of various heart diseases, which can further progress to failure. Heart hypertrophy and failure is a leading cause of death, imposing an enormous burden to the society in the United States. Inhibition of stress induced heart disorders, such as hypertrophy, would be invaluable for prevention and treatment of cardiomyopathy and heart failure.

There exists, therefore, a critical need for new therapies for treatment of oxidative stress induced disorders, including major mental illnesses such as schizophrenia, mood disorders, and addiction, as well as disorders of other organs, such as heart.

SUMMARY OF THE INVENTION

The present inventors performed studies in prefrontal cortex of a model for neuropsychiatric illness using transgenic mice expressing a putative dominant-negative DISC1 (DN-DISC1). In DN-DISC1 mice, pronounced levels of oxidative stress was detected in the prefrontal cortex, but not in the striatum. These mice also displayed greater amounts of GAPDH-Siah1 binding, a protein-protein interaction that is activated under exposure to oxidative stress.

In accordance with an embodiment, the present inventors have found that this oxidative stress has visible behavioral effects in DN-DISC1 mice in vivo, when compared to controls, and that these behavioral effects can be reversed with the compounds and methods of the present invention.

Furthermore, the present inventors investigated the role of oxidative stress in other organ systems. As detailed herein, the inventors found that GAPDH-Siah1 binding was increased in mouse models of cardiac failure. It was also found, that certain novel analogs of deprenyl, significantly inhibited GAPDH-Siah1 binding in cardiac tissue. Thus, with experimental data provided herein, it is clear that this GAPDH-Siah1 binding cascade is a crucial mechanism involved in major mental illness, such as schizophrenia, mood disorders, and addiction, as well as in stress-associated diseases involving other organs where GAPDH is expressed.

Therefore, in accordance with one or more embodiments, the present invention provides novel methods of inhibition GAPDH-Siah1 binding and p300 activation in the cells of a mammal comprising administering to the mammal, a therapeutically effective amount of pharmaceutical compositions comprising various compounds which are structural analogs of the drug deprenyl.

In accordance with an embodiment, the present invention provides a method for inhibition of the GAPDH-Siah1 binding in the cells of a mammal comprising: a) administering to the mammal, a therapeutically effective amount of a composition comprising a compound of formula I,

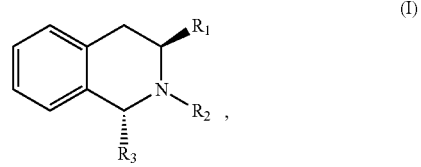

or formula II

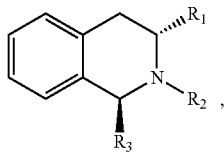
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

In accordance with another embodiment, the present invention provides a method for inhibition of p300 HAT and/or myocyte enhancer factor 2 (MEF) in the cells of a mammal comprising: a) administering to the mammal, a therapeutically effective amount of a composition comprising a compound of formula I,

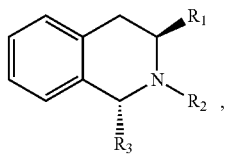
(I)

or formula II

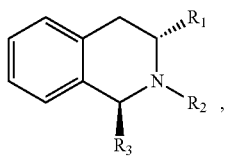
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl and a pharmaceutically acceptable carrier.

In accordance with a further embodiment, the present invention provides a method for inhibition of a stress induced disorder in the brain of a mammal comprising: a) administering to the mammal, a therapeutically effective amount of a composition comprising a compound of formula I,

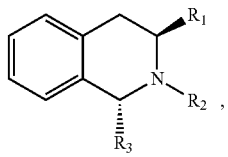
(I)

or formula II

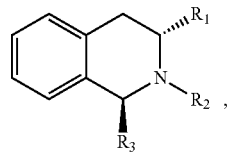
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl and a pharmaceutically acceptable carrier.

In accordance with a further embodiment, the present invention provides a method for inhibition of a stress induced disorder in the brain of a mammal comprising: a) administering to the mammal, a therapeutically effective amount of a composition comprising a compound of formula I,

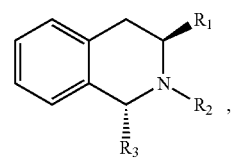
(I)

or formula II

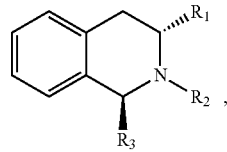
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier; and b) and administering to the mammal, at least one additional therapeutic composition.

In accordance with a further embodiment, the present invention provides a method for inhibition of a stress induced disorder in the organ of a mammal comprising: a) administering to the mammal, a therapeutically effective amount of a composition comprising a compound of formula I,

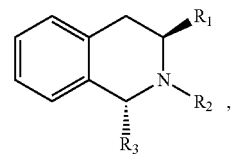
(I)

or formula II

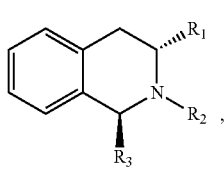
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl and a pharmaceutically acceptable carrier.

In accordance with yet another embodiment, the present invention provides a method for of a stress induced disorder in the organ of a mammal comprising: a) administering to the mammal, a therapeutically effective amount of a composition comprising a compound of formula I,

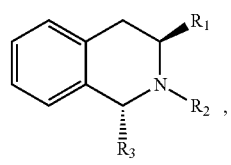
(I)

or formula II

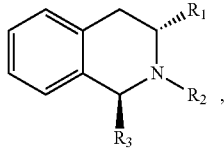
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier; and b) and administering to the mammal, at least one additional therapeutic composition.

In accordance with a further embodiment, the present invention provides a method for inhibition of cardiac hypertrophy in the cardiac cells of a mammal suffering from cardiomyopathy comprising: a) administering to the mammal, a therapeutically effective amount of a composition comprising a compound of formula I,

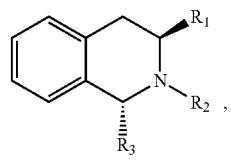
(I)

or formula II

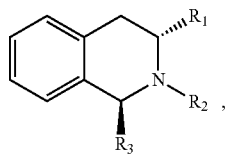
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

In accordance with yet another embodiment, the present invention provides a method for inhibition of cardiac hypertrophy in the cardiac cells of a mammal suffering from cardiomyopathy comprising: a) administering to the mammal, a therapeutically effective amount of a composition comprising a compound of formula I,

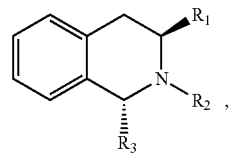
(I)

or formula II

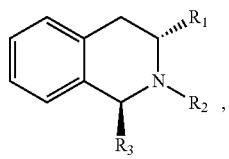
(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier, and b) administering to the mammal, at least one additional therapeutic composition.

BRIEF DESCRIPTION OF THE DRAWINGS

FIG. 3A shows P300-HAT activity in TAC hearts (n=4 in each group). FIG. 3B is a photograph of gross sections (upper panel) of TAC hearts and immunofluorescent staining for GAPDH in cardiac myocytes isolated from TAC hearts. FIG. 3C is a Western blot (upper panels) and quantification (bar graphs, n=6 in each group) using fractionated proteins from TAC hearts.

FIG. 4A shows the chemical structure of (1R,3R)-1,3-dimethyl-2-propargyl-1,2,3,4-tetrahydroisoquinoline (RR compound) in comparison to Deprenyl. FIG. 4B is a graph depicting inhibition of GAPDH-Siah1 binding by the RR compound in vitro. GAPDH was pre-incubated with the RR compound, then GST-Siah1 was added and binding was assessed by GST-agarose pull down followed by western blotting. The graph represents quantification results of the blots from 6 experiments. FIG. 4C is a pair of graphs depicting in vitro MAO activity. FIG. 4D is a bar graph showing glycolytic activity in cultured rat neonatal cardiac cells exposed to 1 nM RR for 48 hours *p<0.05.

FIG. 5A is a photograph of cell lysates immunoprecipitated with Siah1 antibody and probed for GAPDH (upper panel) and quantification results (lower panel, results from 4 experiments) in cardiac myocytes exposed to endothelin) (ET1) in the presence or absence of RR compound. FIG. 5B is a series of photomicrographs showing representative immunofluorescent staining for GAPDH. FIG. 5C is a graph of the quantification results of western blot for GAPDH in nuclear fraction of cardiac myocytes exposed to ET1 in the presence or absence of RR compound. FIG. 5D is a graph of the quantification results of p300 acetylation and MEF2 activity. FIG. 5E are graphs showing the assessment of cardiac myocyte hypertrophy by cell surface area (left), protein synthesis (middle) and hypertrophy gene (BNP). FIG. 5F is a series of photomicrographs showing representative immunofluorescent staining for exogenous GAPDH (HA-tagged) in cardiac cells adenovirally transfected with wild type GAPDH (Ad-GAPDH-WT) or mutant GAPDH (Ad-GAPDH-K227). FIG. 5G is a graph depicting MEF2 activity in cardiac cells transfected with wild type GAPDH (Ad-GAPDH-WT) or mutant GAPDH (Ad-GAPDH-K227) and stimulated with ET1 for 48 hours in the presence or absence of RR compound. FIG. 5H is a graph of BNP mRNA expression *p<0.05.

FIG. 6A is a graph of the quantification results of western blot for GAPDH in nuclear fraction (left) and p300 HAT activity in TAC hearts with vehicle (Veh) or RR (RR) treatment (n=3-4 in each group). FIG. 6B is a series of photomicrographs showing representative cross section hearts (upper panel) and histology (middle panels for Masson Trichrome Staining and lower panels for WGA staining). FIG. 6C is a series of graphs depicting the assessement of cardiac hypertrophy: heart weight normalized by tibia length (left), average cross sectional area of cardiac myocytes (middle) and % fibrosis (right) (n=5-7 in each group). FIG. 6D is an echocardiogram: representative M-mode image (left), fractional shortening (FS) (middle) and left ventricular chamber size at end-diastole (LV-EDD) (right) (n=5-7 in each group). FIG. 6E are three graphs showing comprehensive cardiac functional assessment from invasive pressure-volume loop analysis: representative loops during preload reduction (left), contractile parameter (dPdtmax) (middle) and relaxation parameter (Tau) (right) (n=5-7 in each group). FIG. 6F is a graph showing delayed RR treatment in pre-existing cardiac hypertrophy. Calculated left ventricular mass from echo-cardiogram before (pre-treatment at TAC1W) and after (post-treatment at TAC3W) treatment (left panel) (n=5-7 in each group). left ventricular mass increase over 2 wks (ΔLV mass increase) with vehicle or RR treatment (middle panel) and terminal myocyte size by cross sectional area (CSA) analysis (right) *p<0.05.

FIGS. 8B and 8C depict sulphonated (s) GAPDH staining of cultured rat cardiac myocytes exposed to ET1 with or without RR (B) and a graph of the quantification results (8D). FIG. 8E shows cellular hypertrophy response to ET1 in the absence or presence of RR, assessed by cell surface area, in cells transfected with Ad-GAPDH-WT or with AD-GAPDH-K227 *p<0.05.

FIGS. 9A and 9B are graphs of myocardial mRNA expression levels of BNP and β-MHC (9A) and calcium handling proteins (9B) with n=4 in each group. Supplementary FIG. 9C is a series of graphs depicting hemo-dynamic parameters from PV loop analysis including heart rate, peak left ventricular pressure (LVP), ejection fraction (EF) and power max index (PMI). The latter two parameters are measures for cardiac systolic function. Note that heart rate or afterload (peak LVP) was not affected by the RR compound. n=5-7 in each group. FIG. 9D is a representative cross-section of hearts (left upper panels) and WGA staining (left lower panels) after two weeks treatment with vehicle or RR compound, and myocardial mRNA expression of BNP (right bar graphs). n=4 in each group *p<0.05.

DETAILED DESCRIPTION OF THE INVENTION

Figures 1A, 1B, 1C, 1D:
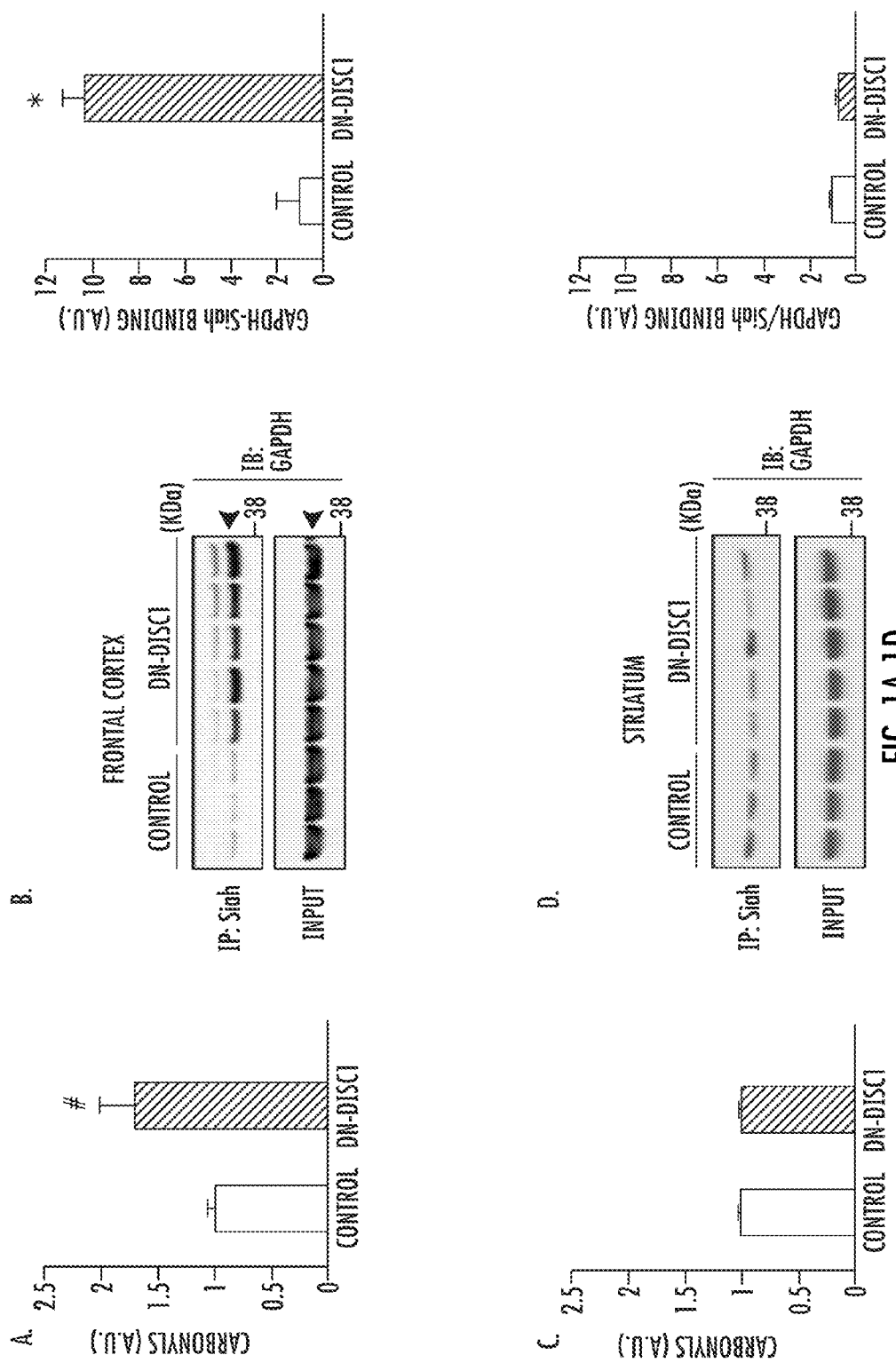
FIG. 1A-1D depict oxidative stress-associated pathology in the frontal cortex. (A) Increased oxidative stress in the frontal cortex of adult DN-DISC1 mice as shown by the carbonyl assay, #p=0.07 (B) Activation of the GAPDH-Siah1 cascade, assayed by GAPDH-Siah1 protein interaction by co-immunoprecipitation, reflects oxidative stress. Augmented activation of this cascade was observed in DN-DISC1 mice, compared with wild-type controls, *p<0.005. Increased oxidative stress was not detected in the striatum by either the carbonyl assay (C) or GAPDH-Siah interaction (D). Error bars indicate SEM.

In accordance with one or more embodiments, the present invention provides novel compounds and methods of GAPDH-Siah1 binding inhibition and p300 activation in the cells of a mammal comprising administering to the mammal, pharmaceutical compositions comprising various compounds which are structural analogs of the drug deprenyl.

In one or more embodiments, the present invention provides a method for inhibition of the GAPDH-Siah1 binding in the cells of a mammal comprising: a) administering to the mammal, a therapeutically effective amount of a composition comprising a compound of formula I,

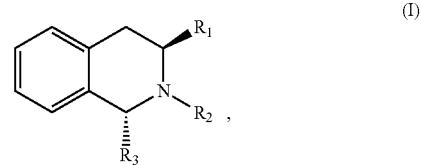

(I)

or formula II

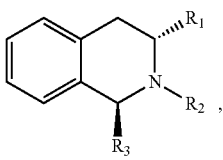

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

In accordance with an embodiment, the present invention provides a pharmaceutical composition comprising a compound of formula I,

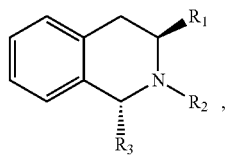

or formula II

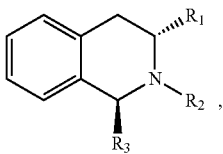

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier in an amount effective for use in a medicament, and most preferably for use as a medicament for inhibition of the GAPDH-Siah1 in the cells of a subject.

In accordance with another embodiment, the pharmaceutical compositions described above can preferably be used as a medicament for inhibition of p300 HAT and/or myocyte enhancer factor 2 (MEF) in the cells of a subject.

In accordance with a further embodiment, the pharmaceutical compositions described above can preferably be used a medicament for inhibition of a stress induced disorder in an organ of a subject.

In some embodiments, the stress induced disorder in an organ of a subject can be in an organ such as the brain or the heart.

"Treating" or "treatment" is an art-recognized term which includes curing as well as ameliorating at least one symptom of any condition or disease. Treating includes reducing the likelihood of a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease; inhibiting the disease, disorder or condition, e.g., impeding its progress; and relieving the disease, disorder or condition, even if the underlying pathophysiology is not affected or other symptoms remain at the same level.

In accordance with one or more embodiments, the diseases or disorders which can be treated with the compounds and methods of the present invention include any disease or disorder which is induced or associated with increased oxidative stress and increased GAPDH-Siah1 binding. In an embodiment, the diseases include major mental illnesses, such as schizophrenia, mood disorders, autism and addiction.

The term "therapeutically effective amount" means the amount of compound or composition administered which is necessary to treat the disease, disorder and/or condition.

"Prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The term "aliphatic" is an art-recognized term and includes linear, branched, and cyclic alkanes, alkenes or alkynes. In certain embodiments, aliphatic groups in the present invention are linear or branched and have from 1-about 20 carbon atoms, preferably about 2 to about 10 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

Substitutions may be made to alkenyl and alkynyl groups to produce, for example, aminoalkenyls, aminoalkynyls, amidoalkenyls, iminoalkenyls, iminoalkynyls, thioalkenyls, thioalkynyls, carbonyl-substituted alkenyls or alkynyls.

With respect to compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

It will be appreciated by one of skill in the art that, in addition to the above-described pharmaceutical compositions, the compositions of the invention can be formulated as inclusion complexes, such as cyclodextrin inclusion complexes, or liposomes.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In one or more preferred embodiments, the route of administration of the above-described pharmaceutical compositions, the composition of the invention is oral.

In addition, in an embodiment, the compositions comprising the above described compounds or derivatives thereof, may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compositions being administered, as well as by the particular method used to administer the composition. Accordingly, there are a variety of suitable formulations of the pharmaceutical compositions of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

As used herein, the term "treat," as well as words stemming therefrom, includes diagnostic and preventative as well as disorder remitative treatment.

In an embodiment, the term "administering" means that the compounds of the present invention are introduced into a subject, preferably a subject receiving treatment for a proliferative disease, and the compounds are allowed to come in contact with the one or more disease related cells or population of cells in vivo.

As defined herein, in another embodiment, the term "contacting" means that the one or more compounds of the present invention are introduced into a sample having at least one cancer cell and appropriate enzymes or reagents, in a test tube, flask, tissue culture, chip, array, plate, microplate, capillary, or the like, and incubated at a temperature and time sufficient to permit binding and uptake of the at least one compound to the cancer cell. Methods for contacting the samples with the compounds, and other specific binding components are known to those skilled in the art, and may be selected depending on the type of assay protocol to be run. Incubation methods are also standard and are known to those skilled in the art.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

An effective amount of compositions of the present invention or derivatives thereof, to be employed therapeutically will depend, for example, upon the therapeutic and treatment objectives, the route of administration, the age, condition, and body mass of the subject undergoing treatment or therapy, and auxiliary or adjuvant therapies being provided to the subject. Accordingly, it will be necessary and routine for the practitioner to titer the dosage and modify the route of administration, as required, to obtain the optimal therapeutic effect. A typical daily dosage might range from about 0.01 mg/kg to up to about 100 mg/kg or more, preferably from about 0.1 to about 10 mg/kg/day depending on the above-mentioned factors. Typically, the clinician will administer antibody until a dosage is reached that achieves the desired effect. The progress of this therapy is easily monitored by conventional assays. In some embodiments, the dosage of the compounds of the present invention are from about 0.1 mg/kg/day to about 10 mg/kg/day, preferably about 0.2 mg/kg/day to about 0.5 mg/kg/day. In a preferred embodiment, the dosage is about 0.25 mg/kg/day.

The dosage ranges for the administration of compositions described above or derivatives thereof, are those large enough to produce the desired effect in which the symptoms of the disease are ameliorated, or the enzymatic activity or binding is inhibited.

The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication.

In accordance with an embodiment, the present invention provides a method for inhibition of p300 HAT and/or MEF in the cells of a mammal comprising: a) administering to the mammal, a therapeutically effective amount of a composition comprising a compound of formula I,

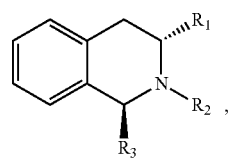

or formula II

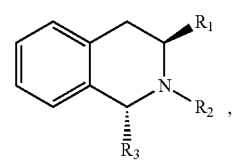

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

In accordance with a further embodiment, the present invention provides a method for inhibition of a stress induced disorder in the brain of a mammal comprising: a) administering to the mammal, a therapeutically effective amount of a composition comprising a compound of formula I,

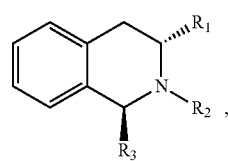

or formula II

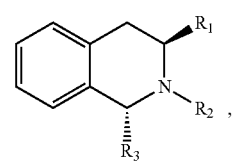

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

In accordance with a still another embodiment, the present invention provides a method for inhibition of a stress induced disorder in the brain of a mammal comprising: a) administering to the mammal, a therapeutically effective amount of a composition comprising a compound of formula I, (I)

or formula II

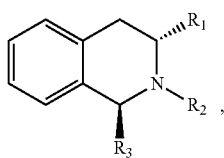

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier; and b) and administering to the mammal, at least one additional therapeutic composition.

In accordance with a further embodiment, the present invention provides method for inhibition of a stress induced disorder in the organ of a mammal comprising: a) administering to the mammal, a therapeutically effective amount of a composition comprising a compound of formula I,

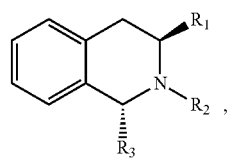

or formula II

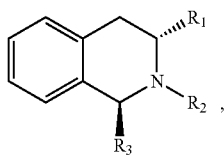

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

In accordance with a further embodiment, the present invention provides a method for inhibition of a stress induced disorder in the brain of a mammal comprising: a) administering to the mammal, a therapeutically effective amount of a composition comprising a compound of formula I,

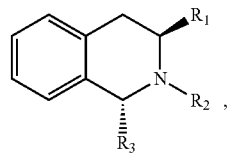

or formula II

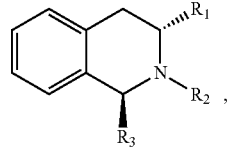

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier; and b) and administering to the mammal, at least one additional therapeutic composition.

In accordance with yet another embodiment, the present invention provides a method for of a stress induced disorder in the organ of a mammal comprising: a) administering to the mammal, a therapeutically effective amount of a composition comprising a compound of formula I,

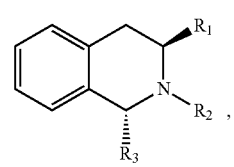

or formula II

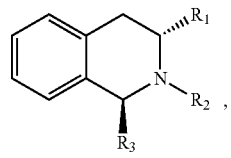

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier; and b) and administering to the mammal, at least one additional therapeutic composition.

As used herein, the term "stress induced disorders" include those which arise when an organism is placed in an environment that disrupts its homeostasis. Events such as illness, disease, life-threatening events, starvation, fatigue, etc. are all understood to be stressors on an organism.

In accordance with one or more embodiments, the stress induced disorders treated by the compounds and methods of the present invention are those which are associated with GAPDH-Siah1 binding and also associated with increased p300 expression.

In other examples, the etiology of major mental illnesses such as schizophrenia, mood disorders, autism and addiction are been thought to be a result, in part, of stressors on the brain, including, for example, the adolescent brain.

In DN-DISC1 mice, pronounced levels of oxidative stress were detected in the prefrontal cortex, but not in the striatum. These mice also displayed greater amounts of glyceraldehyde-3-phosphate dehydrogenase binding with Siah1, a protein-protein interaction that is activated under exposure to oxidative stress. In DN-DISC1 mice, behavioral deficits were observed in well-defined tests for the cognitive control of adaptive behavior using reversal learning and reward devaluation paradigms. For example, DN-DISC1 mice display various behavioral abnormalities including impaired social recognition as demonstrated by no preference for a stranger mouse over a familiar mouse in the three chamber social novelty test (Johnson et al., Proc. Natl. Acad. Sci. USA, 2013; 110(30):12462-7). Thus, in accordance with one or more embodiments, the term "stress induced disorders" include many types of major mental illnesses, including, for example, mood disorders, schizophrenia, autism and addictions. Thus, one of ordinary skill in the art would understand that the compositions and methods provided herein can be useful in treating stress induced disorders of the brain as described above.

Stressors can induce cortisol and epinephrine, which can have deleterious effects on organs, including, for example, the heart, and the brain. Stressors can cause various physical manifestations—e.g., asthma, back pain, arrhythmias, fatigue, headaches, irritable bowel syndrome, ulcers, and suppress the immune system. Stress induced disorders, as used herein, also include heart disease, including cardiac hypertrophy. Thus, one of ordinary skill in the art would understand that the compositions and methods provided herein can be useful in treating stress induced disorders in the heart and other organs.

In accordance with another embodiment, the present invention provides a method for inhibition of cardiac hypertrophy in the cardiac cells of a mammal suffering from cardiomyopathy comprising: a) administering to the mammal, a therapeutically effective amount of a composition comprising a compound of formula I,

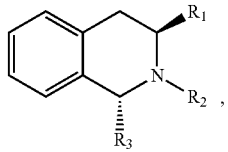

or formula II

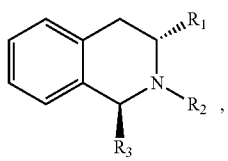

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

As used herein, the term "cardiac hypertrophy" or "pathological hypertrophy" means a thickening of the heart muscle (myocardium) which results in a decrease in size of the chamber of the heart, including the left and right ventricles. A common cause of cardiac hypertrophy is high blood pressure (hypertension) and heart valve stenosis.

As used herein, the term "cardiomyopathy" refers to diseases of the heart muscle and/or the measurable deterioration of the function of the myocardium for any reason. These diseases have many causes, signs and symptoms, and treatments. As cardiomyopathy worsens, the heart becomes weaker. The heart is less able to pump blood through the body and maintain a normal electrical rhythm. This can lead to heart failure or irregular heartbeats called arrhythmias. In turn, heart failure can cause fluid to build up in the lungs, ankles, feet, legs, or abdomen.

In accordance with a further embodiment, the present invention provides a method for inhibition of cardiac hypertrophy in the cardiac cells of a mammal suffering from cardiomyopathy comprising: a) administering to the mammal, a therapeutically effective amount of a composition comprising a compound of formula I,

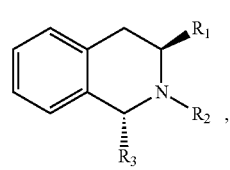

or formula II

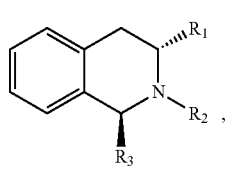

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier; and b) and administering to the mammal, at least one additional therapeutic composition.

As used herein the term "pharmaceutically active compound" or "therapeutically active compound" or "therapeutic composition" means a compound or composition useful for the treatment or modulation of a disease or condition in a subject suffering therefrom. Examples of pharmaceutically active compounds can include any drugs known in the art for treatment of disease indications. In a preferred embodiment, the additional therapeutic compositions are those indicated for diseases of the heart. Examples of such compounds include, without limitation, α-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class I antiarrhythmics, class antiarrhythmics, class antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, thrombolytic agents, angiotensin II receptor blockers, digoxin, digitoxin, diuretics, and aldosterone antagonists.

In another preferred embodiment, the additional therapeutic compositions are those indicated for relief of stress, such as sedatives (also referred to as tranquilizers, hypnotics, and/or anxiolytics), antidepressants, and barbiturates. In some embodiments, the therapeutic composition can comprise psychotropic agents, such as antidepressants, heterocyclic antidepressants, monoamine oxidase inhibitors, selective serotonin re-uptake inhibitors, tricyclic antidepressants, anti-manics, anti-psychotics, phenothiazine antipsychotics, anxiolytics, sedatives, and hypnotics, barbiturate sedatives and hypnotics, benzodiazepine anxiolytics, sedatives, and hypnotics, and psychostimulants.

In accordance with an embodiment, the present invention provides a compound of formula I:

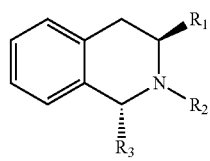

(I)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl.

In accordance with an embodiment, the present invention provides a compound of formula II:

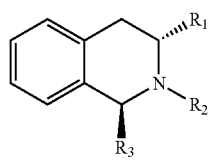

(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl.

In another embodiment, the present invention provides compound of formula I, wherein the compound is:

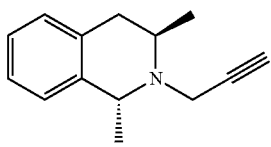

((1R, 3R)-1, 3-dimethyl-2-propargyl-1, 2, 3, 4-tetrahydroisoquinoline).

In a further embodiment, the present invention also provides a pharmaceutical composition comprising a compound of formula I,

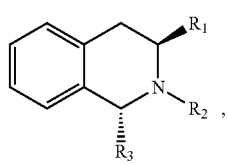

(I)

or formula II

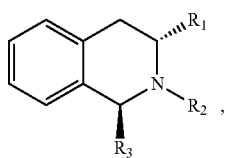

(II)

wherein $R_1$ to $R_3$ can be the same or different, and can include H, OH, $C_2$-$C_8$ alkyl, $C_2$-$C_8$, alkenyl, $C_2$-$C_8$ alkynyl, substituted $C_2$-$C_8$ alkyl, $C_2$-$C_8$, alkenyl, and $C_2$-$C_8$ alkynyl, and a pharmaceutically acceptable carrier.

One of ordinary skill in the art would understand that the above described compounds and compositions can be administered together with one or more additional therapeutic agents, either simultaneously or within a specified period of time either pre-, or post-administration of the compounds and compositions of the present invention.

EXAMPLES

Reagents: All reagents were purchased from Sigma, unless noted otherwise.

Cardiac animal models: All protocols were approved by Animal Care and Use Committee of the Johns Hopkins University. TAC was performed in C57/BL6 mice (Jackson Laboratory) as previously described in (*Nat. Med.*, 11, 214-222 (2005), *J. Clin. Invest.*, 119, 408-420 (2009), *J. Am. Coll. Cardiol.*, 56, 2021-2030 (2010)).

DN-DISC1 mice express a putative dominant-negative C-terminal truncated $DISC_1$ under expression control of the α CaMKII promoter. Homozygous DN-DISC1 mice were created by systematic cross-breeding of heterozygotes followed by interbreeding of homozygotes at the Johns Hopkins School of Medicine. In the current studies only homozygous males were used. At 3 to 6 months of age, mice were transferred to the Neurogenetics and Behavior Center, Johns Hopkins University, for behavioral testing. They were housed three or four to a cage under a 12 hour light/dark cycle (lights on at 7:00 A.M to 7:00 P.M) and weighed between 25 and 35 grams prior to food deprivation.

Physiological analysis, histological analysis: Echocardiography and pressure-volume loop studies were performed as described previously (Takimoto et al., Nat. Med., 11, 214-222 (2005)). 10% formalin fixed heart samples were embedded in paraffin, sectioned and stained for myocyte size (WGA staining) and fibrosis (Masson Trichrome staining) as described previously (Zhang et al., J. Am. Coll. Cardiol., 56, 2021-2030 (2010)). Isolated adult cardiac myocyte or rat neonatal cardiac myocyte was fixed with 50% methanol/50% acetone and stained with antibodies against GAPDH (Millipore), sulphonated GAPDH or HA as previously described.

Rat neonatal cardiac myocyte culture: Rat neonatal cardiac myocytes (RNCM) were isolated from 1-2-day-old Sprague-Dawley rats, and cultured cells stimulated with 0.05 μM Endothelin-1, with or without 1 nM RR compound for 48 hours. Protein synthesis was assessed by [$^3$H]leucine incorporation. Adenoviral transfection of wild-type GAPDH and K227A mutant GAPDH was performed at 10-30 moi as previously described.

HAT activity assay, MEF2 activity assay, MAO activity assay, GAPDH assay: p300 HAT activity was measured using commercially available kit (Biovision), using immunoprecipitation with p300 antibody (Circulation 118, 934-946 (2008)). MEF2 activity was measured using luciferase reporter assay (Panomics). MAO activity assay was measured using commercially available kit (Peninsula Laboratory). GAPDH activity was measured as previously described in (*Nat. Cell Biol.*, 7, 665-674 (2005)). PUMA mRNA expression was determined by real time RT-PCR using SYBR Green fluorescence on a LightCycler instrument (Roche Applied Science). Expression of the gene of interest was divided by the housekeeping gene glyceraldehyde-3-phosphate dehydrogenase (GAPDH) and presented as fold induction of control.

Protein and RNA analysis: Total RNA was isolated from cells or left ventricular myocardium with Trizol (Molecular Research Center, Inc, Cincinnati, Ohio) and analyzed by real-time polymerase chain reaction (PCR) with TaqMan probes (Applied Biosystems, Foster City, Calif.). Results were normalized to GAPDH or 18S RNA. Cell lysates or nuclear extracts were obtained from cultured myocytes or ventricular tissue, resolved by SDS-polyacrylamide gel electrophoresis, subjected to immunoblotting and imaged by chemiluminescence as previously described.

Assessment of oxidative stress: Two methods were used to assess oxidative stress in prefrontal cortex and in striatum. For a general measurement a dot blot procedure was used with the OxyBlot™ Protein Oxidation Detection Kit (Millipore S7150), which immunodetects carbonyl groups that arise from oxidized proteins. This experiment was conducted with young adult DN-DISC1 mice (n=7) and wild type control mice (n=8). To look specifically at the glyceraldehyde-3-phosphate dehydrogenase (GAPDH)-Siah1 interaction, coimmunoprecipitation by precipitation was performed with anti-Siah1 antibodies (Santa Cruz SC-5506) and immunoblot with anti-GAPDH antibodies (AbD Serotec). This experiment was conducted with young adult DN-DISC1 mice (n=5) and C57 control mice (n=3), with young adult DN-DISC1 mice (n=5), and C57 control mice (n=3).

Measurement of Social Novelty Test: Wt and DN-DISC1 mice were treated with RR compound or control starting at postnatal day 35 (0.25 mg/kg, i.p./day) and continuing throughout the three-chamber social interaction test in adulthood as described in Johnson et al., supra.

Statistical analysis: Data are shown as mean±SEM. Multiple group comparison was performed by one-way analysis of variance followed by the Bonferroni procedure for comparison of means.

Example 1

Oxidative stress-associated pathology in the cortex of the brain.

The previous behavioral findings suggest dysfunction to prefrontal circuitry and are consistent with decreased immunoreactivity of parvalbumin in interneurons of the medial prefrontal cortex in DN-DISC1 mice. To extend our assessment of pathology to prefrontal circuitry, we used methods to examine the presence of oxidative stress affecting prefrontal networks in DN-DISC1 mice. We first examined a gross measurement using a protein carbonyl assay in which irreversible oxidative modification of proteins was quantified. Here we observed a trend towards an increase in oxidative modification in DN-DISC1 mice compared with wild-type controls (FIG. 1A; p=0.07). To address possible downstream signaling elicited by oxidative stress, we focused on glyceraldehyde-3-phosphate dehydrogenase (GAPDH). Under exposure to excess oxidative stress GAPDH is post-translationally modified at a specific cysteine residue, C150, which enables GAPDH to bind with Siah1 which has a strong nuclear localization signal. GAPDH-Siah1 complex then translocates to the nucleus where it can affect epigenetic and transcriptional machinery. Thus, the levels of GAPDH-Siah1 protein interaction can be utilized to monitor the activation of this signaling cascade elicited by oxidative stress. An almost 10-fold up-regulation of GAPDH-Siah1 binding was observed in DN-DISC1 mice compared to controls (FIG. 1B; p<0.01). Notably, these changes in oxidative modification and GAPDH-Siah1 binding were localized to the prefrontal cortex but not observed in the striatum (FIGS. 1C,D; p's>0.05).

Example 2

Preliminary results for treatment of psychiatric disorders in a mouse model using the compounds of the present invention.

Figure 2:
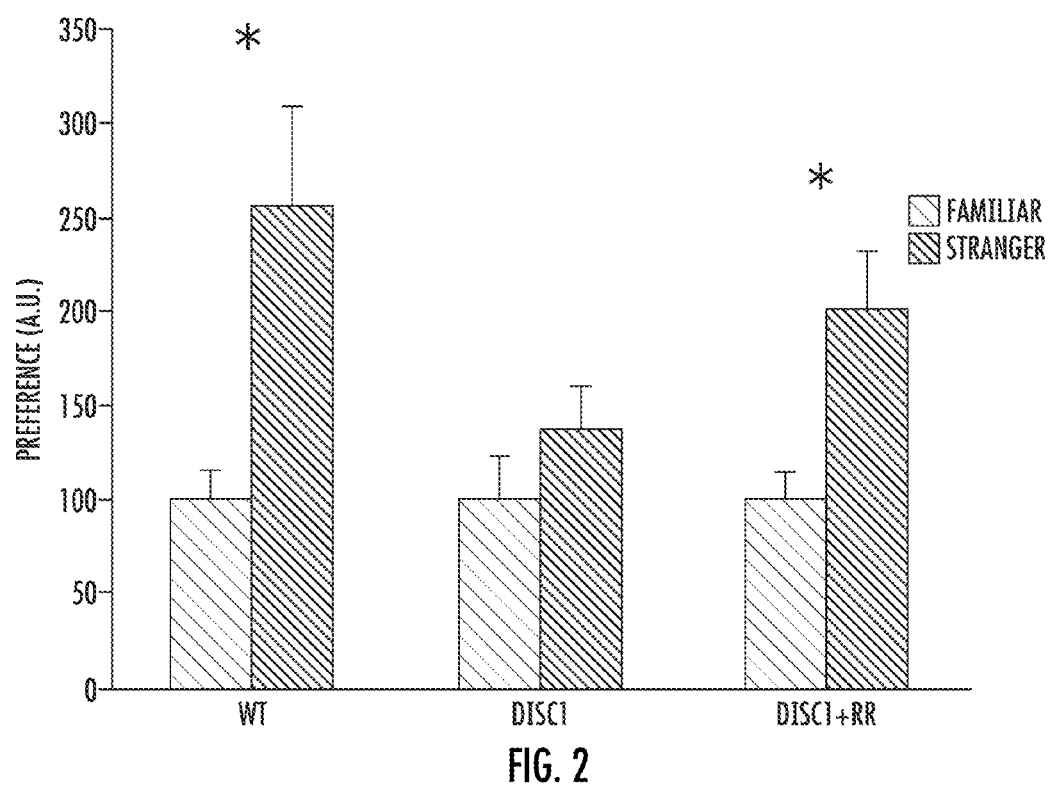
FIG. 2 depicts a social novelty test in the three chamber social interaction paradigm. WT (n=5) and DISC1 mice treated with RR (n=7) preferentially sniffed the stranger mouse over the familiar mouse, whereas $DISC_1$ mice did not (n=3). *p<0.05.

The inventors have previously shown that DN-DISC1 mice display various behavioral abnormalities including impaired social recognition as demonstrated by no preference for a stranger mouse over a familiar mouse in the three chamber social novelty test (Johnson et al., supra). The inventors treated DN-DISC1 mice with RR starting at postnatal day 35 (0.25 mg/kg, i.p./day) and continuing throughout the three-chamber social interaction test in adulthood. It was found that RR treatment ameliorated the social deficit under these conditions (FIG. 2).

Example 3

To understand the pathology underlying heart hypertrophy, chronic pressure overload induced by transverse aorta constriction (TAC) is used as an established experimental animal model. Heart hypertrophy is evident at 7 to 10 days after the constriction, which leads to irreversible functional defects in 9 weeks. In the present study, the TAC model was employed and identified GAPDH as a key conveyer of the pathological stress signal to nuclear p300, resulting in disruption of critical homeostasis in vivo.

Figures 3A, 3B, 3C:
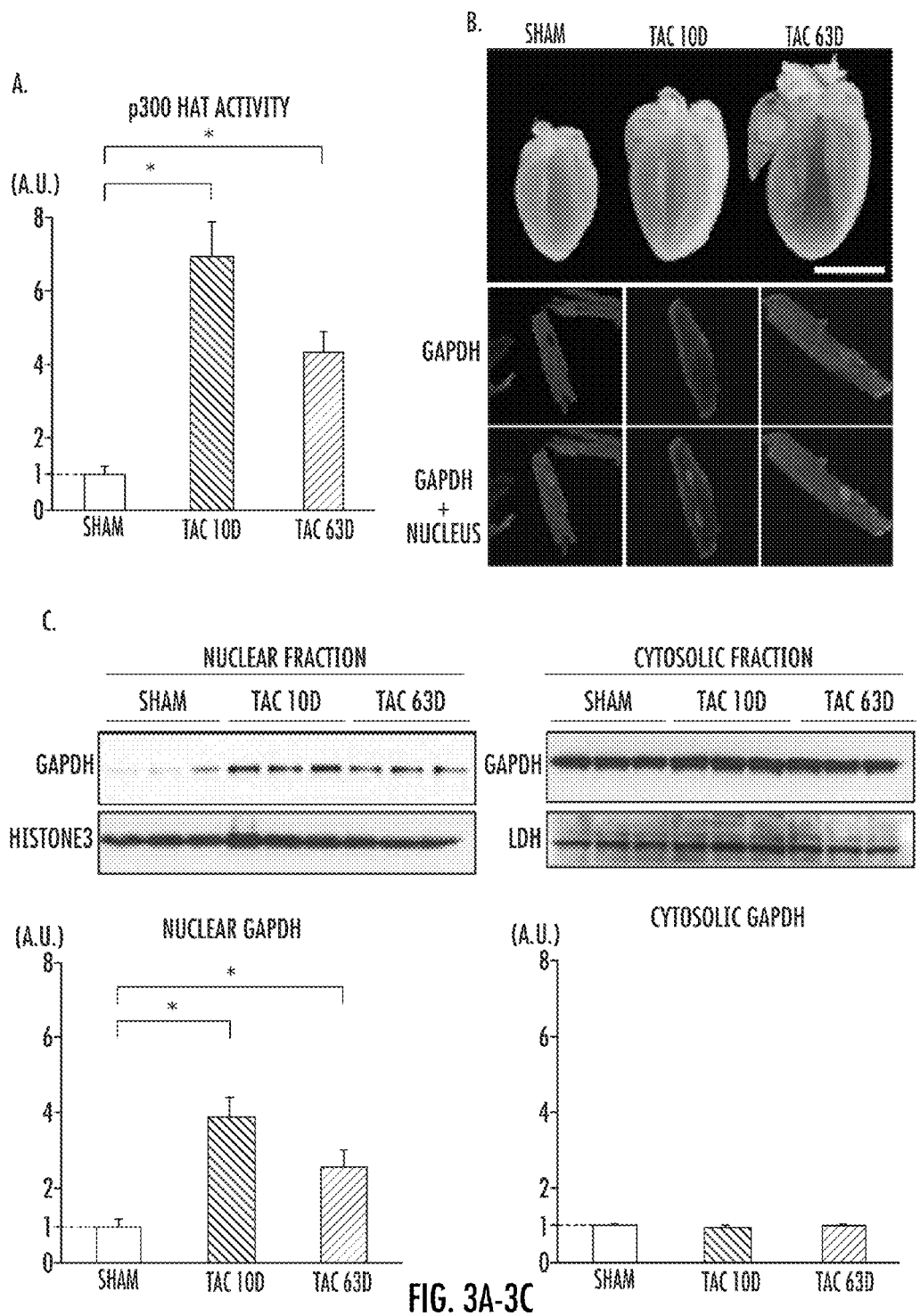
FIG. 3A-3C illustrate the augmented p300 HAT activity and nuclear accumulation of GAPDH in hypertrophied hearts exposed to chronic pressure-overload (TAC).

To elucidate a homeostatic control of heart hypertrophy, it was determined whether the HAT activity of p300 was altered in TAC hearts in vivo, and it was found that the activity was dramatically increased 10 days after the constriction was implemented (TAC 10D), which remained high when tested again 63 days later (FIG. 3A).

Example 4

Figure 7:
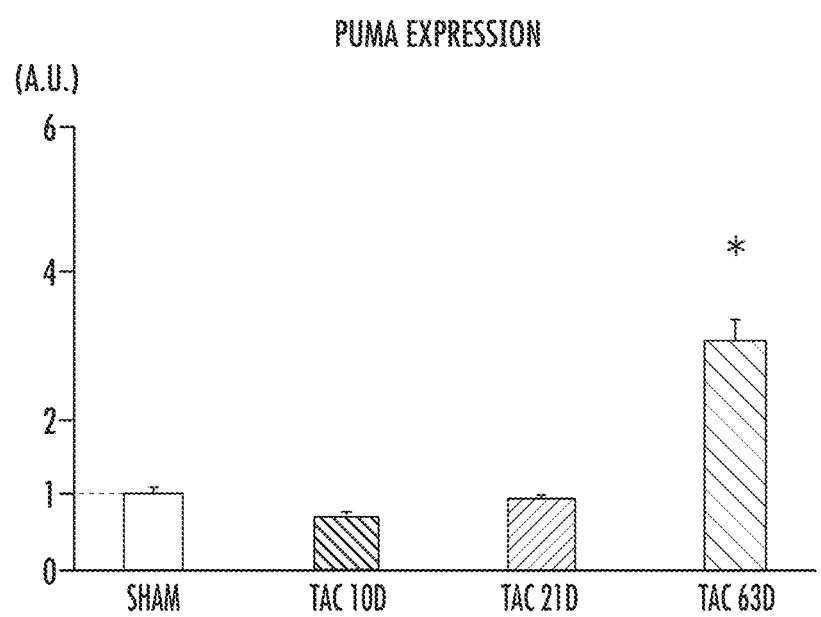
FIG. 7 depicts expression of p53 upregulated modulator of apoptosis (PUMA) in sham and TAC treated hearts (at 10 days, 21 days, and 63 days) in vivo, as measured by RT-PCR *p<0.05.

As the inventors previously reported that nuclear translocated GAPDH could activate p300 at least in culture cells, such as RAW264.7 cells, subcellular localization of GAPDH in the TAC heart was examined. Nuclear accumulation of GAPDH was evident by immunostaining in cardiac myocytes isolated from TAC treated hearts at 10 and 63 days post treatment, which was absent in those myocytes isolated from hearts with the sham operation (FIG. 3B). To confirm this observation, the inventors quantitatively assessed nuclear GAPDH in the heart tissues by biochemical subcellular fractionation (FIG. 3C). GAPDH in the nuclear fraction was increased in TAC treated hearts at both time points, but not in sham hearts, while GAPDH in cytosol fraction was unaltered in all conditions. These results are consistent with the present invention that TAC elicits nuclear translocation of GAPDH followed by activation of p300, which is an underlying mechanism for heart hypertrophy. This is further supported by the fact that expression of PUMA was unchanged in TAC-treated hearts at 10 days after constriction (FIG. 7), indicating that the mechanism involving nuclear GAPDH in the TAC heart is different from that in the brain.

Example 5

Figures 4A, 4B, 4C, 4D:
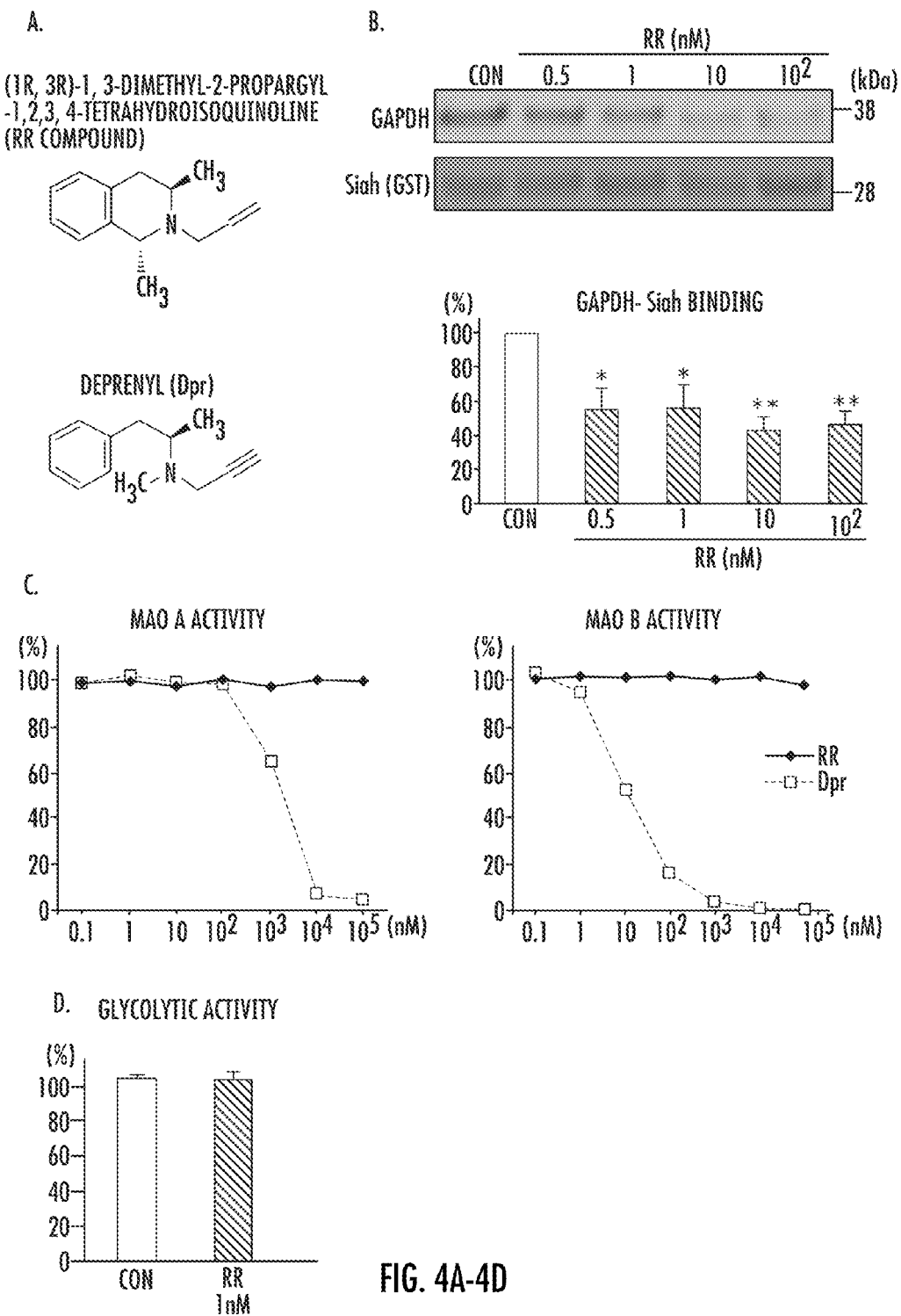
FIG. 4A-4D depict a deprenyl derivative compound of the present invention that blocks GAPDH-Siah1 binding.

To test whether TAC elicits nuclear translocation of GAPDH and activates p300, a specific tool to intervene GAPDH nuclear translocation is needed. Several structural analogues of deprenyl that blocked GAPDH-Siah1 binding and the nuclear GAPDH cascade were previously screened (data not shown). One of the most potent compounds was RR (FIG. 4A). During in vitro binding experiments with purified recombinant GAPDH and GST-Siah1 proteins, RR blocked the interaction at nanomolar concentrations (FIG. 4B).

Example 6

A major challenge to identify a compound that selectively blocks the nuclear GAPDH cascade is their potential inhibition of monoamine oxidases (MAOs), which deprenyl originally harbors. Thus, it was examined whether RR inhibits MAO-A/B in cultured myocytes and a dramatic contrast was observed between RR and deprenyl. There was no inhibition of MAOs by RR in a wide range of concentrations between 0.1 nM and $10^5$ nM concentrations (FIG. 4C). In addition, RR did not show any influence on GAPDH glycolytic activity in cardiac myocytes at 1 nM (FIG. 4D), the dose that was employed in the subsequent studies. In summary, it was found that RR is a compound that can block GAPDH-Siah1 protein interaction potently, and with high specificity, without affecting MAO activity and GAPDH glycolytic activity.

Example 7

Figure 8A:
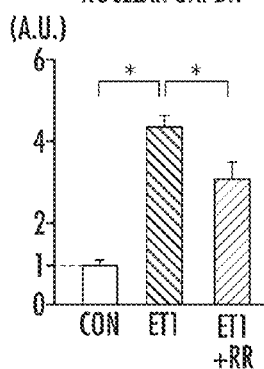
FIG. 8A-8E. 8A is a graph of quantification results of GAPDH staining (representative staining in FIG. 4A). Ratios of average intensity in the nucleus to that in cytosol for GAPDH are shown. About 30 cells were analyzed in each group.
Figure 8B:
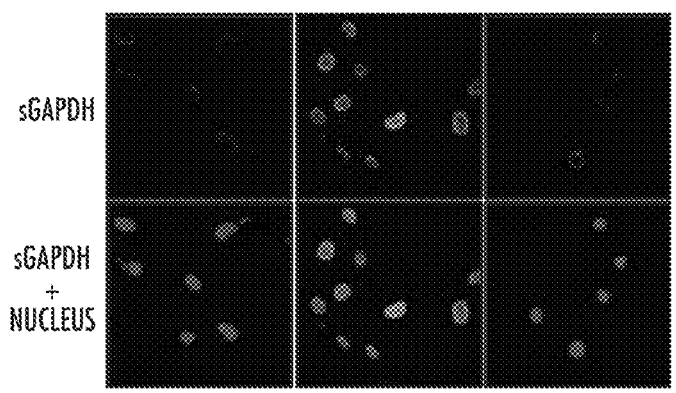
Figure 8C:
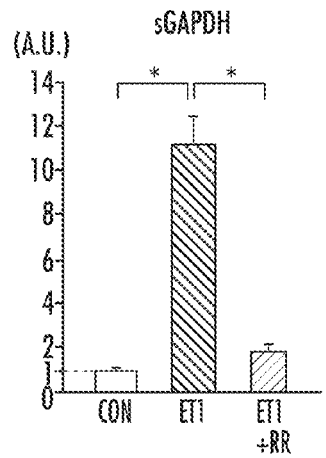

To test a role for the GAPDH-p300 signaling in heart hypertrophy, the Gq agonist ET1 was used as a trigger. ET1 is reported to elicit oxidative stress by activating NADPD oxidase and stress is known as a central contributor to cardiac hypertrophic response including pressure-load hypertrophy, as in the TAC model. Thus, cardiac myocytes were exposed to ET1 at 0.05 µM for about 48 hours and the effects on GAPDH signaling was examined. GADPH-Siah1 binding was augmented following ET1 administration and normalized by co-administration of RR. Both immunofluorescent cell staining and biochemical fractionation indicated that nuclear translocation of GAPDH occurred in response to ET1 (FIGS. 5A, B; FIG. 8A). Co-treatment with RR compound at 1 nM blocked augmented the nuclear translocation (FIGS. 5B, C; FIG. 8A). Consistent with the translocation, accumulation of sulphonated GAPDH and augmentation of p300 acetylation (reflecting p300 HAT activity) were observed in the nucleus, both of which were blocked by co-treatment with the RR upon ET1 exposure (FIGS. 8B, C).

Example 8

Figures 5A, 5B, 5C, 5D, 5E, 5F, 5G, 5H:
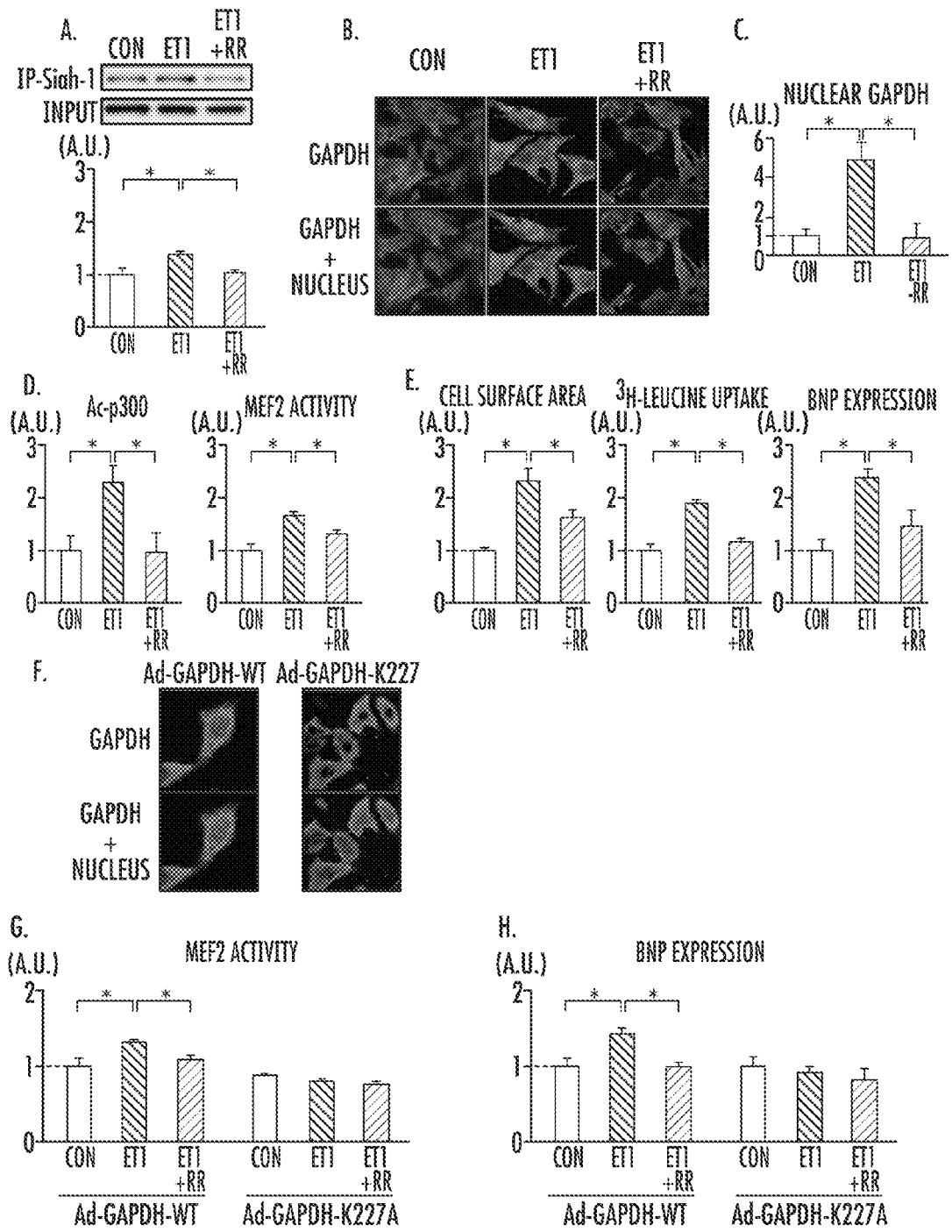
FIG. 5A-5H depict the role of GAPDH nuclear cascade in cardiac cellular hypertrophy.
Figure 8D:
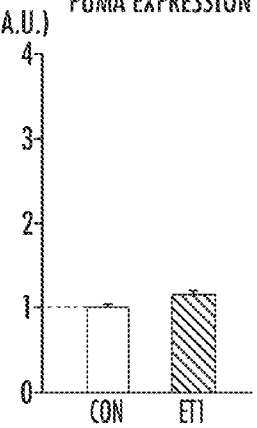

Augmented p300 activity reportedly leads to cardiac hypertrophic response via activation of myocyte enhancer factor 2 (MEF2), a master transcriptional factor of maladaptive cardiac hypertrophy. Thus, acylation of p300, and activity of MEF2 was tested, together with several outcome measures for hypertrophy response. In cardiac myocytes treated with ET1, augmentation of p300 acylation (reflecting p300 HAT activity), an augmented activity of MEF2, and increases in cell surface area, protein synthesis assayed by $^3$H-leucine uptake, and B-type natriuretic peptide (BNP) expression were observed (FIGS. 5D, E). Very importantly, all of these changes were clearly blocked by the RR compound at 1 nM (FIGS. 5D, E) while PUMA expression was unchanged (FIG. 8D). These results provide pharmacologically evidence that the GAPDH-p300-MEF2 cascade, which is independent of PUMA-mediated cell death, plays a crucial role in cardiac hypertrophic response.

Example 9

Figure 8E:
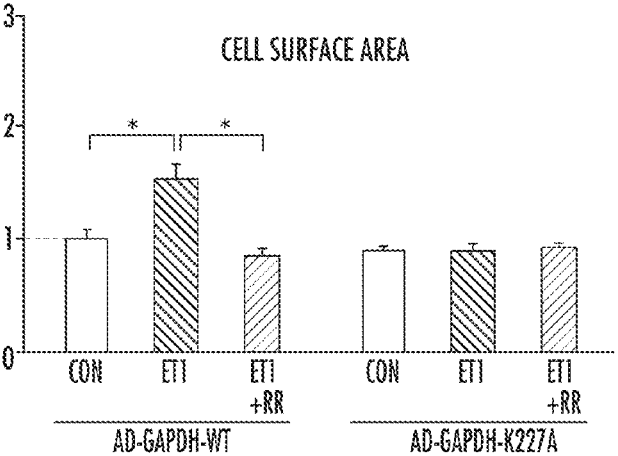

To further validate this mechanism, molecular intervention was also studied. Nuclear translocation of GAPDH is mediated by interaction of Siah1, and one crucial lysine residue K227 in human, K225 in rat) of GAPDH is responsible for the protein interaction. Expression of the mutant GAPDH with the substitution of this lysine residue interferes with endogenous GAPDH binding with Siah1, and functions as a dominant-negative in this cascade. Thus, it was first confirmed that this dominant-negative human GAPDH-K227 stayed in the cytoplasm in cardiac myocytes under exposure to ET1 (FIG. 5F). Consistent with the pharmacological intervention, the expression of this dominant-negative GAPDH blocked the augmentation of MEF2 activity (FIG. 5G) and outcome measures for cardiac hypertrophic response, including an increase in BNP expression (FIG. 5H; FIG. 8E).

Example 10

In the present invention, the significance of the nuclear GAPDH cascade in vivo has been shown. With this understanding there is also provided novel therapeutic methods of treatment of stress induced disorders, including, for example, cardiac hypertrophy, which are urgent and very important medical needs. The TAC model shows that augmentation of p300 HAT activity and GAPDH nuclear translocation was demonstrated (FIG. 3). Daily administration of the RR compound (0.25 mg/kg/day i.p.) started simultaneously, at the time of constriction, dramatically reduced the levels of p300 HAT activity and nuclear GAPDH, when measured after the $10^{th}$ day of administration (TAC10) (FIG. 6A).

Figures 6A, 6B, 6C, 6D, 6E, 6F:
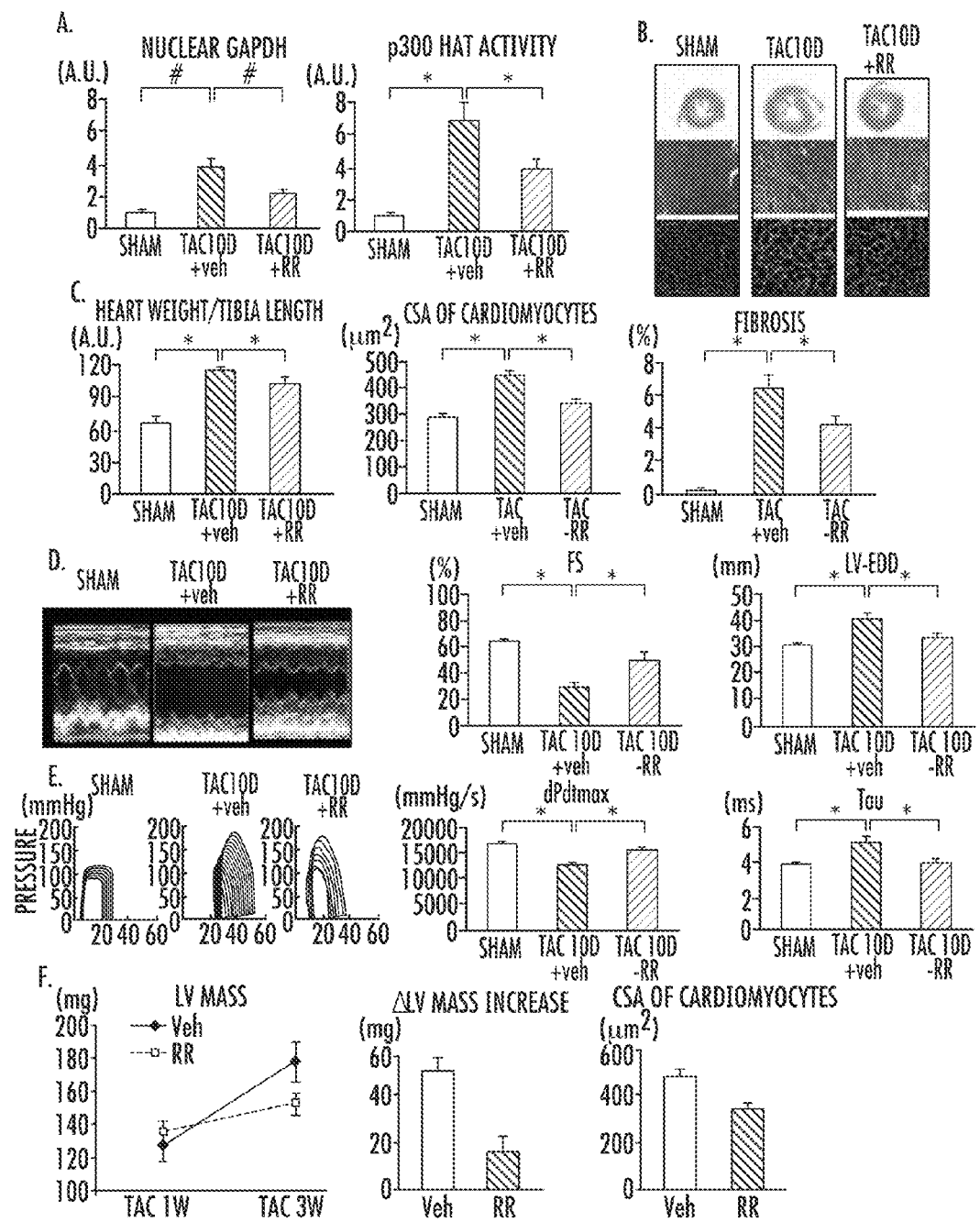
FIG. 6A-6F depict the in vivo role of GAPDH nuclear cascade in cardiac hypertrophy, remodeling and function.
Figures 9A, 9B, 9C, 9D:
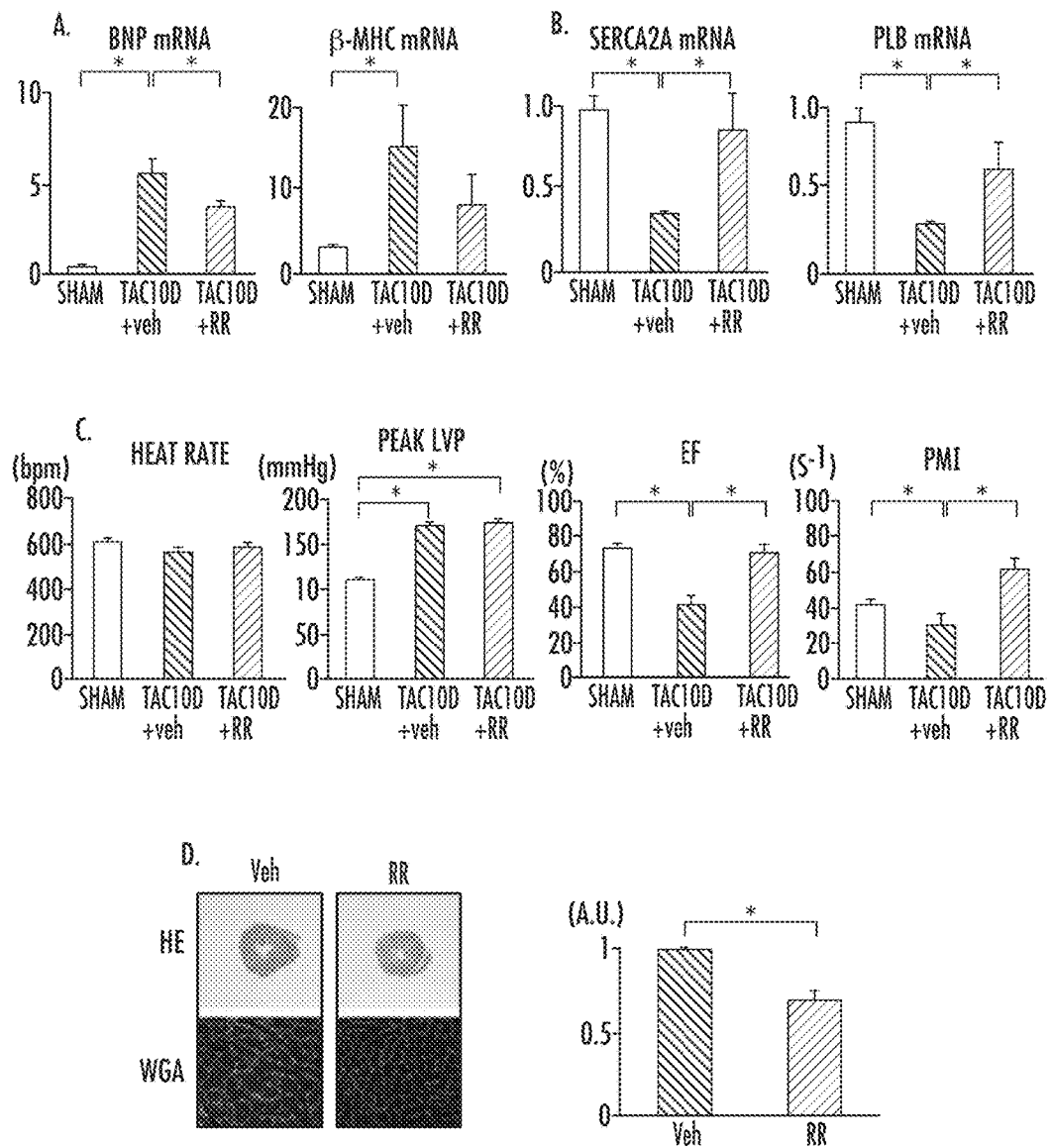
FIG. 9A-9D.

Consistent with the notion obtained from studies with cardiac myocytes (FIG. 5), the drug administration ameliorated cardiac hypertrophy remodeling, which was assessed by heart weight, cardiac myocyte cell size, and fibrosis in vivo (FIGS. 6B, C). The pathological gene expression profile was also significantly improved or normalized, and which included fetal gene re-expression (FIG. 9A) and down-regulation of calcium handling proteins (FIG. 9B). Most importantly, these anti-remodeling effects are also associated with ameliorated cardiac function. Cardiac function by echocardiogram showed that the RR compound significantly inhibited TAC-induced reduction in Fractional Shortening (% FS, a measure reflecting systolic function) and left ventricular dilatation (LV-EDD, Left ventricular end-diastolic dimension) (FIG. 6D). Invasive hemodynamic study was also performed using pressure volume loop analysis, demonstrating improvement of cardiac performance despite sustained pressure-overload stress (FIG. 6E representative loop tracings on left, parameter bar graphs on right; FIG. 9C). Both systolic function (dPdtmx) and diastolic relaxation properties (Tau) were significantly better in hearts with RR treatment than that with vehicle treatment (FIG. 6E). These results indicate that the RR compound is effective in blocking the nuclear GAPDH cascade and resultant changes in stress induced disorders, and in particular, cardiac hypertrophy and function in vivo.

Example 11

In most clinical settings, medication and treatment starts only after pathological changes occur at least to some extent. Thus, to prove whether the RR treatment of the present invention has potential for translation, the efficacy of RR treatment initiated 1 week after induction of pressure load was examined, when left ventricular (LV) mass estimated by echocardiogram showed over 50% increase (about 120-130 mg) versus sham control (FIG. 6F, left). About two weeks of RR treatment significantly blocked further LV mass increase from sustained pressure overload (FIG. 6F, middle). Terminal postmortem assessment revealed that RR treatment resulted in smaller cardiac myocyte size (FIG. 6F, right). Consistent with these observations, a significant improvement was also found in the expression profile of cardiac fetal gene (BNP) in the RR-treated group compared with the vehicle group (FIG. 9D). These results suggest that the RR compound and the methods of the present invention have high potential in the treatment of established cardiac hypertrophy.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for inhibition of GAPDH-Siah1 in the cells of a subject comprising administering to the subject an effective amount of a pharmaceutical composition comprising a compound of formula I,

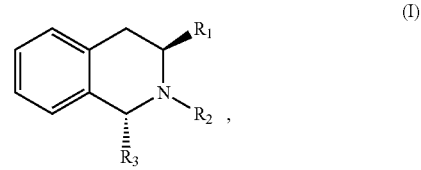

or formula II

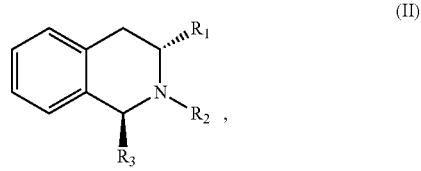

wherein $R_1$ and $R_3$ can be the same or different, and can include H, OH, $C_2$-$C_8$ alkyl, $C_2$-$C_8$, alkenyl, $C_2$-$C_8$ alkynyl, and $R_2$ is $C_2$-$C_8$ alkynyl, and wherein when $R_1$ and $R_3$ are both alkyl, $R_1$ and $R_3$ cannot both have a cis or both have a trans conformation, and a pharmaceutically acceptable carrier.

* * * * *